US010512423B2

(12) United States Patent
Yin et al.

(10) Patent No.: US 10,512,423 B2
(45) Date of Patent: Dec. 24, 2019

(54) DETERMINING ENERGY EXPENDITURE OF A USER

(75) Inventors: Bin Yin, Eindhoven (NL); Paulus Henricus Antonius Dillen, I, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 401 days.

(21) Appl. No.: 13/144,379

(22) PCT Filed: Jan. 11, 2010

(86) PCT No.: PCT/IB2010/050085
§ 371 (c)(1),
(2), (4) Date: Jul. 13, 2011

(87) PCT Pub. No.: WO2010/084430
PCT Pub. Date: Jul. 29, 2010

(65) Prior Publication Data
US 2011/0276304 A1    Nov. 10, 2011

(30) Foreign Application Priority Data

Jan. 21, 2009    (EP) .................................. 09150987

(51) Int. Cl.
*A61B 5/11*    (2006.01)
*A61B 5/00*    (2006.01)

(52) U.S. Cl.
CPC .......... *A61B 5/1118* (2013.01); *A61B 5/4866* (2013.01); *A61B 2562/0219* (2013.01)

(58) Field of Classification Search
None
See application file for complete search history.

(56) References Cited

U.S. PATENT DOCUMENTS 7,028,547 B2    4/2006   Shiratori et al.
2003/0074157 A1*  4/2003   Westerterp et al. .......... 702/141
(Continued)

FOREIGN PATENT DOCUMENTS

EP    1219238 A1    7/2002
EP    1252862 A1    10/2002
(Continued)

OTHER PUBLICATIONS

Choi et al., "Estimation of Activity Energy Expenditure: Accelerometer Approach" Proceedings of the 2005 IEEE Engineering in Medicine and Biology 27th Annual Conference, Shanghai, China, Sep. 1-4, 2005, pp. 3830-3833.*
(Continued)

*Primary Examiner* — John C Kuan (57) ABSTRACT

The invention relates to an electronic device for estimating energy consumption of a person. The electronic device uses a mathematical model based on acceleration data for estimating the person's energy consumption as a function of the actual performed activity and acceleration values. The acceleration values are converted to an estimate of energy consumption of a given activity by scaling a value of time integrated acceleration data with an activity scaling parameter. The activity scaling parameters for different activities have been determined off-line by comparing measured energy consumptions over e.g. a day with estimated energy consumptions over the same period, where the estimated values are determined using the mathematical model.

13 Claims, 3 Drawing Sheets

(56) References Cited

U.S. PATENT DOCUMENTS

| | | | |
|---|---|---|---|
| 2005/0107723 A1 | 5/2005 | Wehman | |
| 2007/0238938 A1* | 10/2007 | Nishibayashi et al. | 600/301 |
| 2008/0281234 A1* | 11/2008 | Goris et al. | 600/595 |
| 2009/0264789 A1* | 10/2009 | Molnar et al. | 600/544 |
| 2010/0274100 A1* | 10/2010 | Behar et al. | 600/301 |

FOREIGN PATENT DOCUMENTS

| | | |
|---|---|---|
| EP | 1302162 A2 | 4/2003 |
| EP | 1836956 A2 | 9/2007 |
| JP | 08131425 A | 5/1996 |
| JP | 08317920 A1 | 12/1996 |
| JP | 2001258870 A | 9/2001 |
| JP | 2005230340 A | 9/2005 |
| WO | 2004032715 A2 | 4/2004 |
| WO | 2008071840 A1 | 6/2008 |

OTHER PUBLICATIONS

Chen et al., "Improving energy expenditure estimation by using a triaxial accelerometer" Journal of Applied Physiology 83:2112-2122, 1997.*

Plasqui et al. "Measuring Free-Living Energy Expenditure and Physical Activity with Triaxial Accelerometry" Obesity Research vol. 13 No. 8 Aug. 2005, pp. 1363-1369.*

Bonomi et al., "Improving assessment of daily energy expenditure by identifying types of physical activity with a single accelerometer" Journal of Applied Physiology 107: 655-661, 2009.*

Crouter et al., "Estimating energy expenditure using accelerometers" Eur J Appl Physiol (2006) 98:601-612.*

Kim et al: "Estimation of Activity Energy Expenditure Based on Activity Classification Using Multi-Site Triaxial Accelerometry"; Electronics Letters, vol. 44, No. 4, Feb. 14, 2008, pp. 266-267.

Bouten et al: "A Triaxial Accelerometer and Portable Data Processing Unit for the Assessment of Daily Physical Activity"; IEEE Transactions on Biomedical Engineering, vol. 44, No. 3, Mar. 1997, pp. 136-147.

M.J. Mathie et al, "Accelerometry: providing an integrated, practical method for long-term, amulatory monitoring of human movement", Physiol, Meas., 2004-25:R1-R20.

* cited by examiner

DETERMINING ENERGY EXPENDITURE OF A USER

FIELD OF THE INVENTION

The present invention relates to determining energy expenditure of a user, and in particular to improving determination of energy expenditure of different activities.

BACKGROUND OF THE INVENTION

Monitoring of humans energy expenditure during a day is used in devices for medical, healthcare and consumer lifestyle applications.

Known devices for measuring energy expenditure use motion sensors attached to a person's thigh or waist. By analyzing sensor outputs, energy expenditures of e.g. running or walking can be determined. However, such methods have shown to give less accurate measures of energy expenditure for certain activities such as cycling.

EP 1302162 discloses an exercise amount measuring device comprising an acceleration sensor for detecting a body movement of a living body, means for calculating an exercise amount based on a detection signal of the acceleration sensor, and a display section for displaying the calculated exercise amount, said device further comprising: means for calculating an estimated consumption calorie value representing consumption of energy in a prescribed period; and a display section for displaying the calculated estimated consumption calorie value.

Whereas EP 1302162 discloses a device for estimating energy consumption during a prescribed period, it is questionable whether the device is capable of determining the consumed energy of different activities such as cycling with sufficient accuracy. Accordingly, it is an object of the present invention to improve the estimation of energy expenditures of different types of activities.

It should be noted that paper "estimation of activity energy expenditure based on activity classification using multi-site triaxial accelerometry", Kim D. et Al., Electronics Letters, IEE stevenage, GB, vol. 44, no. 4, 14 Feb. 2008, pages 266-267, XP006030492 ISSN:0013-5194, describes a wireless networked multi-site triaxial accelerometry system to estimate activity energy expenditure during daily life. A feature of the system is the utilization of activity classification based on multi-site acceleration signals. The signal processing and estimation algorithm, uses the integral of absolute values of accelerometer output. These values were then converted to estimate activity energy expenditure using a linear regression equation based on reference data obtained using a standard method. Activity during a given period was automatically classified into two categories, i.e. arm-dominant and leg-dominant activities, according to the ratio of wrist to ankle acceleration signal amplitudes. This ratio was incorporated into the regression analysis as an additional factor.

Further, it should be noted that paper "A triaxial accelerometer and portable data processing unit for the assessment of daily physical activity", Carlijn V. C. Bouten et al., IEEE transactions on biomedical engineering, IEEE service center, Piscataway, N.J., US, vol. 44, no. 3, 1 Mar. 1997, XP011006346 ISSN:0018-9294, describes the development of a triaxial accelerometer (TA) and a portable data processing unit for the assessment of daily physical activity. The TA is composed of three orthogonally mounted uniaxial piezoresistive accelerometers and can be used to register accelerations covering the amplitude and frequency ranges of human body acceleration. The data unit enables the on-line processing of accelerometer output to an estimator of physical activity over eight-day periods. Further, it should be noted that WO 2004/032715 (Bodymedia Inc.) 22 Apr. 2004, describes a method and apparatus for measuring a state parameter of an individual using signals based on one or more sensors. In one embodiment, a first set of signals is used in a first function to determine how a second set of signals is used in one or more second functions to predict the state parameter. In another embodiment, first and second functions are used where the state parameter or an indicator of the state parameter may be obtained from a relationship between the first function and the second function. The state parameter may, for example, include calories consumed or calories burned by the individual.

SUMMARY OF THE INVENTION

Accordingly, the invention preferably seeks to alleviate or eliminate one or more of the above mentioned disadvantages of incorrect estimations of energy expenditures. In particular, it may be seen as an object of the present invention to provide a device that provides improved estimations of different types of energy expenditures.

This object and several other objects are obtained in a first aspect of the invention by providing a device for determining an energy expenditure of a user, the device comprising
a data input for receiving acceleration data of the user as a function of time,
a parameter input for receiving one or more user parameters $U_i$ characterizing the user,
a storage for storing constant parameters and activity scaling parameters, the scaling parameters being a function of an activity of the user, the activity being obtained as a user-input or being determined by an automatic activity recognition algorithm,
a processor for determining an activity value in dependence of activity by integrating or summing the acceleration data over the duration of an activity, and for determining an estimated value of energy expenditure by obtaining a product of the activity scaling parameters and the activity value and by forming a sum of said product and the one or more user parameters, where the user parameters are scaled by the constant parameters and the duration of the activity.

The invention is particularly, but not exclusively, advantageous for obtaining a device for determining energy expenditures of activities performed by a user of the device.

It may be advantageous to calculate activity value from acceleration data of a given activity performed by a person or user since the acceleration data provides an indication of the energy expenditure of the activity.

It may be seen as a further advantage to obtain a measure of the energy expenditure by multiplying the activity value with an activity scaling parameter since the scaling parameters are a function of an activity of the user and, therefore, may scale the activity value to provide an improved measure of the energy expenditure. Indeed, the activity scaling parameter may correct activity values which overestimates or underestimates the energy expenditure of the actual activity performed by the user. Accordingly, scaling of the acceleration based activity counts may be advantageous since this enables the user to better distinguish between the intensity levels of different activities and may, therefore, motivate the user to exercise activities having otherwise underestimated energy expenditures since the energy consumptions of such activities may be determined with greater accuracy.

It is understood that summing the acceleration data may comprise summing magnitudes of the acceleration data.

In an embodiment the activity scaling parameters k(p) may have been determined by minimizing a difference between a measured energy expenditure value obtained for a given period comprising one or more activities and a sum of values of the estimated energy expenditure values for activities over the same period.

It may be advantageous to determine activity scaling parameters k(p) by minimizing a difference between a measured energy value, which is considered the correct value, and an energy value that has been estimated using the scaling parameters k(p), since both values are for the same period of time so that the determined scaling parameters k(p) provides an improved estimate of energy for the entire period.

The embodiment for determining activity scaling parameters k(p) may also be used for determining other constant parameters ai.

In an embodiment determining the activity scaling parameters (k(p)) may comprise obtaining a plurality of data pairs of measured energy expenditure values and acceleration data of a plurality of subjects, where the energy expenditure values and acceleration data are measured over a given period, minimizing the difference between measured energy expenditure values and calculated energy expenditure value obtained using a model to determine the activity scaling parameters, where the model determines activity count values from the acceleration values by integrating or summing the acceleration data over the duration of an activity to obtain values of activity count, multiplying values of activity count with the activity scaling parameters and summing products of activity count and the activity scaling parameters over activities.

It may be an advantage to obtain the plurality of data pairs of measured energy expenditure values and acceleration data of a plurality of subjects so that the determined activity scaling parameters provides improved estimates of energy expenditures for different subject, e.g. persons of different weight and age.

In an embodiment the activity scaling parameters may be greater than a preset threshold value for activities having activity values determined from the acceleration data which underestimates the actual energy expenditure, and where the activity scaling parameters may be smaller than the threshold value for activities having activity values determined from the acceleration data which overestimates the actual energy expenditure.

The preset threshold may be any value such as the value one.

In an embodiment the processor is further configured for forming a sequence of estimated values of energy expenditure for different activities to determine a time profile of the energy expenditure, e.g. a profile for the period of a day.

It may be advantageous to provide the estimated energy expenditure values as a sequence in index and order of the performed activities in order to provide the user with an overview of energy expenditures for different activities performed during a period, for example during a day.

Since the sequence of values of energy expenditures are determined using activity scaling parameters that have been determined by constraining the total estimated energy expenditure for a given period to be the same as the measured and correct energy expenditure of the same period, the total energy expenditure given by the sequence approximates the measured energy expenditure with good accuracy.

In an embodiment the user parameters comprises age, weight and height, and the sum of said product and user parameters are scaled by the constant parameters and the duration of an activity according to the equation: $PAEE(p)=Tp*a0'+Tp*a1'*age+Tp*a2'*weight+Tp*a3'*height+a4*k(p)*AC(p)$, where the sum additionally comprises the term $Tp*a0'$.

In an embodiment, determining the activity value in dependence of activity comprises integrating or summing the acceleration data over the duration of an activity for each acceleration direction of the acceleration sensor.

It may be advantageous to integrate acceleration data, e.g. magnitudes of acceleration data, for each axis or direction of the acceleration sensor to provide more reliable values of energy expenditure.

A second aspect of the invention relates to a method for manufacturing the device according to the first aspect comprising, obtaining a plurality of data pairs of measured energy expenditure values and acceleration data of a plurality of subjects, where the energy expenditure values and acceleration data are measured over a given period, minimizing the difference between measured energy expenditure values and calculated energy expenditure values obtained using a model for calculating a value of energy expenditure of activities in a recursive loop to determine the constant user parameters and the activity scaling parameters, where an activity value of the model is determined from acceleration data of a given activity from a given subject by integrating or summing the acceleration data, providing the determined constant parameters and the activity scaling parameters in a device.

It may be seen as an advantage to determine the constant user parameters and the activity scaling parameters from a plurality of data pairs of measured energy expenditure values and acceleration data of a plurality of subjects since the determined parameters may provide improved accuracy due to the use of experimental data of a plurality of subjects. The parameters may be provided in a device according to the first aspect. For example, the parameters may be stored in a memory of the device during manufacturing.

In an embodiment of the second aspect, the step of minimizing comprises, in a recursive loop performing of steps a-c:

a) in a model (PAEE_CAL(j)) for calculating a value of energy expenditure of activities (p), obtaining an activity count value for each data pair of each user, where the activity count value is obtained from the expression $\Sigma_p k(p)*AC(p)$ by summing the product of activity scaling parameters and activity values over activities in a period, where the activity value is determined from acceleration data of a given activity from a given subject, b) using the model, determining the constant parameters by comparing the measured energy expenditure value with the calculated energy expenditure value, and c) adjusting activity scaling parameters for given activities until the difference between the measured energy expenditure value and the calculated energy expenditure value is below a given threshold.

Adjusting the activity scaling parameters may comprise adjusting the activity scaling parameters that are defined by a set of intervals according to pre-set step sizes until a set of parameters is found that minimizes the difference between the measured energy expenditure values and the calculated energy expenditure values.

A third aspect of the invention relates to a system for determining an energy expenditure of a user, the system comprising the device according to the first aspect and a transportable accelerometer for measuring acceleration data of the user.

The transportable accelerometer may be connectable to the device according to the first aspect via a wired or wireless connection, or the accelerometer and the device may be integrated into a single system component.

A fourth aspect of the invention relates to a method for determining an energy expenditure of a user, comprising obtaining an activity (p) performed by a user (101) as a user-input or by an automatic activity recognition algorithm, determining an activity value in dependence of activity performed by a user, by integrating or summing acceleration data of the user over the duration of the activity, selecting an activity scaling parameter from a set of scaling parameters according to the actual activity, the scaling parameters being a function of an activity of the user, determining an estimated value of energy expenditure by obtaining a product of the activity scaling parameter and the activity value and by forming a sum of said product and one or more user parameters, where the user parameters are scaled by the constant parameters and the duration of the activity, and where the user parameters characterizes the user.

A fifth aspect of the invention relates to a computer program product enabling a computer processor to carry out the method of the fourth aspect.

The first, second, third, fourth and fifth aspect of the present invention may each be combined with any of the other aspects. These and other aspects of the invention will be apparent from and elucidated with reference to the embodiments described hereinafter.

In summary, the invention relates to an electronic device for estimating energy consumption of a person. The electronic device uses a mathematical model based on acceleration data for estimating the person's energy consumption as a function of the actual performed activity and acceleration values. The acceleration values are converted to an estimate of energy consumption of a given activity by scaling a value of time integrated acceleration data with an activity scaling parameter. The activity scaling parameters for different activities have been determined off-line by comparing measured energy consumptions over e.g. a day with estimated energy consumptions over the same period, where the estimated values are determined using the mathematical model.

BRIEF DESCRIPTION OF THE FIGURES

The present invention will now be explained, by way of example only, with reference to the accompanying Figures, where.

DETAILED DESCRIPTION OF AN EMBODIMENT

Figure 1A:
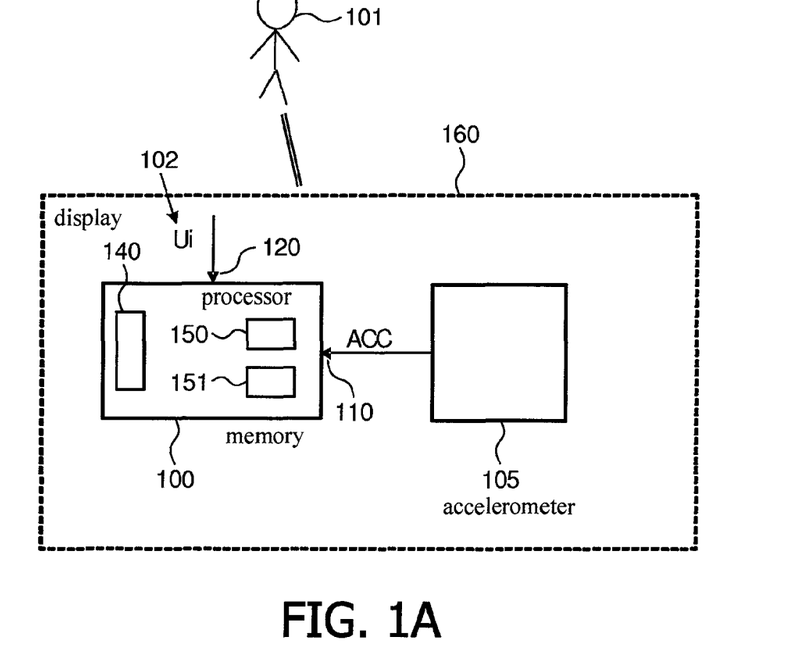
FIG. 1A shows a device and system for determining a user's energy expenditure.

FIG. 1A shows a device 100 for determining an energy expenditure of a user 101 on basis of acceleration data ACC provided from an associated accelerometer 105 via a data input 110. The acceleration data is in the form of an analogue or digital time dependent signal. The device 100 further comprises a parameter input 120 for receiving user parameters Ui characterizing the user 101 which carries the accelerometer 105. The device 100 comprises data storage 151 for storing constant parameters ai and activity scaling parameters k(p) (to be explained below). A processor 150, for example a digital processing unit, comprised by the device 100 is used to process acceleration data, user parameters Ui, constant parameters ai and activity scaling parameters k(p) to determine energy expenditure of a user 101. Graphical profiles and values of the energy expenditure determined by the processor 150 may be displayed on a display 140 comprised by the device 100.

The accelerometer 105 may be carried by the user 101. When the user wishes to inspect an energy expenditure profile or values, the user may connect the device 100 to the accelerometer for transferring accelerometer data stored in the accelerometer 105 to the device 100.

Alternatively, both the energy expenditure determining device 100 and the accelerometer 105 may be carried by the user during use of the device 100 so that the accelerometer 105 continuously transfers acceleration data ACC to the device 100.

The energy expenditure determining device 100 and the accelerometer 105 may be comprised by a system 160 as individual components or the device 100 and the accelerometer may be integrated into a single integrated device 160.

Figure 1B:
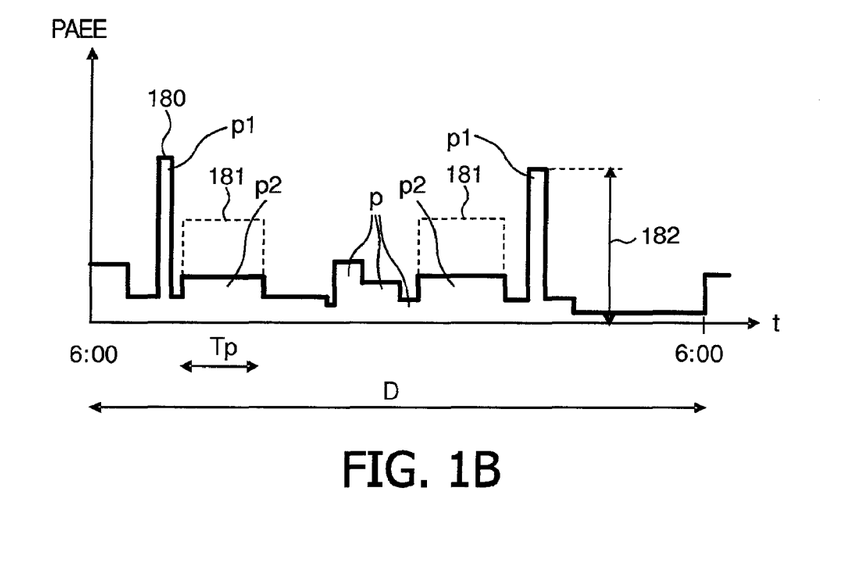
FIG. 1B shows estimated energy expenditure values and an energy expenditure profile.

FIG. 1B shows an estimated one-day energy expenditure profile 180 of a user, for example a human or an animal. The profile 180 shows the user's physical activity in terms of energy expenditure PAEE as a function of time t. Different activities p shows different levels of energy expenditure of physical activity PAEE. For example activities p1 due to a user's walking may have relative high levels of physical activity energy expenditure PAEE compared to other activities p performed during a period D, for example a day measured from 6:00 AM to 6:00 AM the next day. The user in FIG. 1A also performs cycling twice that day, as illustrated by activity p2. However, the level of PAEE is underestimated for activity p2 since the actual amount of energy expenditure is higher as illustrated by the dotted line 181.

The energy expenditure profile 180 is determined from acceleration values from an accelerometer carried by the user of FIG. 1. However, the cycling activity p2 results in small acceleration values compared to for example walking or running since first of all cycling does not involve direct impact with ground that contributes greatly to the generation of accelerations especially along a direction vertical to the ground; secondly, unlike walking or running, cycling creates little movement of the upper body in both vertical and horizontal directions, leading to a limited level of accelerations when an accelerometer is worn at the waist or chest. Accordingly, use of acceleration values for cycling and other activities may give incorrect estimations of energy expenditure profiles 180 as compared to actual energy expenditure profiles 181 measured using for example a gold standard method such as the doubly-labeled water (DLW) method by determining the washout kinetics of injected hydrogen and oxygen isotopes.

The actual activity p performed by the user 101 may be provided to the device 100 by a user-input (not shown) by which the user may input an activity, e.g. using activity buttons, a keyboard or a touch sensitive display. Alternatively, the activity may be determined by an automatic activity recognition algorithm processed by the processor 150. The automatic activity recognition algorithm may utilize data from a GPS sensor (Global Positioning System) carried by the user, data from a heartbeat sensor, a blood pressure sensor and a microphone. For example, the activity p may be determined from velocity information provided by the GPS and heartbeat information provided by the heartbeat sensor. The automatic activity recognition algorithm may also utilize acceleration data ACC to automatically determine the actual activity. For example, low acceleration values combined with a GPS measure of a high velocity, e.g. above 20 km/h, may be recognized as cycling.

Physical activity related energy expenditure PAEE may be determined from acceleration measurements using various methods. Equation 1 below provides one method for estimating PAEE from acceleration measurements:

$$PAEE = a0 + a1*age + a2*weight + a3*height + a4*ACD, \quad \text{eq. 1}$$

where a0-a4 are constant parameters and the factors age, weight and height are user characteristic parameters. The coefficients a0-a4 may be gender-dependent, so eq. 1 may be different for males and females.

The factor ACD represents an activity count per day and is determined from acceleration data of the user carrying an accelerometer. The accelerometer used may provide acceleration data in one direction, for example in Earth gravity direction, in two perpendicular directions or in all three perpendicular directions. The activity count per day ACD may be determined by integrating or summing the acceleration data from the accelerometer. When the accelerometer has more than one accelerometer direction, the activity count per day ACD may be determined from the acceleration data by summing integrated magnitudes of the acceleration data obtained for each acceleration direction, where integration is performed over a given period of acceleration data, for example one day of acceleration data. For example the following equation, $$ACD = \Sigma_n \Sigma_{ti} |ACC(ti)_n|$$

equates ACD by summing magnitudes of acceleration samples ACC over the sampling index ti and summing over each direction n of the accelerometer. When the acceleration signal is an analogue signal, the summation over samples ti can be replaced by integration over time.

Since the derivation of PAEE from eq. 1 does not distinguish between different activities p, the values of PAEE for different activities may be under- or overestimated since the acceleration values used for calculation of ACD does not correctly represent the actual energy expenditure of different activities p. For example, low acceleration values of cycling may underestimate the PAEE value of cycling.

Values of physical activity related energy expenditure PAEE may be determined by scaling acceleration data or the ACD value according to the type of activity p associated with acceleration data in order to more accurately estimate energy expenditure profiles 180 for different types of physical activities p. Equation 2 below uses activity scaling parameters k(p) for scaling acceleration data according to the type of activity:

$$PAEE(p) = Tp*a0' + Tp*a1'*age + Tp*a2'*weight + Tp*a3'*height + a4*k(p)*AC(p) \quad \text{eq. 2}$$

In general the constant parameters a0', a1', a2', a3' are given as a rate of change per time and, therefore, a0', a1', a2', a3' are multiplied with the duration Tp of the activity p in order to determine the energy expenditure for an activity p. Thus, Tp is a function of the actual activity p. The last term in eq. 2 is multiplied with the constant parameter a4 which is not given as a rate of change per time since AC(p) is already determined for the duration Tp. Accordingly, the last term is not multiplied with Tp.

When the constant parameters a0-a4 of eq. 1 are equated to give a one-day PAEE value in eq. 1, the equivalent rate of change in time of a0 (or a1-a3) may be given by a0'=a0/D, where D may be the duration of a day given in minutes.

Thus, in eq. 2, instead of using an activity count per day ACD which integrates accelerations of different activities, an activity value AC(p) obtained from acceleration values for different activities p and scaled by the activity dependent parameters (k(p)) is used.

It is understood that equation 2 gives a value or height 182 of an activity p of the PAEE time profile 180.

Accordingly, the entire PAEE profile 180 of one or more activities p within a period D can be determined by forming a sequence of PAEE values 182 for each activity p1,p2 up to pm as follows $$PAEE(p1,p2, \ldots ,pm) = \{PAEE(p1), PAEE(p2), \ldots ,PAEE(pm)\}. \quad \text{eq. 3}$$

The activity value AC(p) in eq. 2 is determined by integrating or summing magnitudes of acceleration data obtained from an acceleration sensor carried by the user. When the acceleration sensor has multiple sensor directions n, the activity value AC(p) is determined from the acceleration data by summing integrated, summed or averaged magnitudes of the acceleration data ACC(ti) obtained for each acceleration direction. The activity value AC(p) is obtained by integrating, summing or averaging data ACC(ti) over the duration of each activity p. As an example, the activity value AC(p) may be determined from:

$$AC(p) = \Sigma_n \Sigma_{ti} |ACC(ti)_n|,$$

where magnitudes of acceleration values ACC of a given activity p are summed over sampling times ti and over each direction n of the accelerometer for the duration of the activity p. When the acceleration signal ACC is an analogue signal, the activity value AC(p) is obtained by integrating the magnitude of the acceleration signal over time t. It is understood that sampling times ti or continuous times t are given as functions of activities p and, therefore, AC(p) becomes a function of activity p.

Calculation of the activity value AC(p) from acceleration values ACC may include removing acceleration components due to Earth gravity, e.g. by filtering away the DC component of the acceleration values.

Figure 2A:
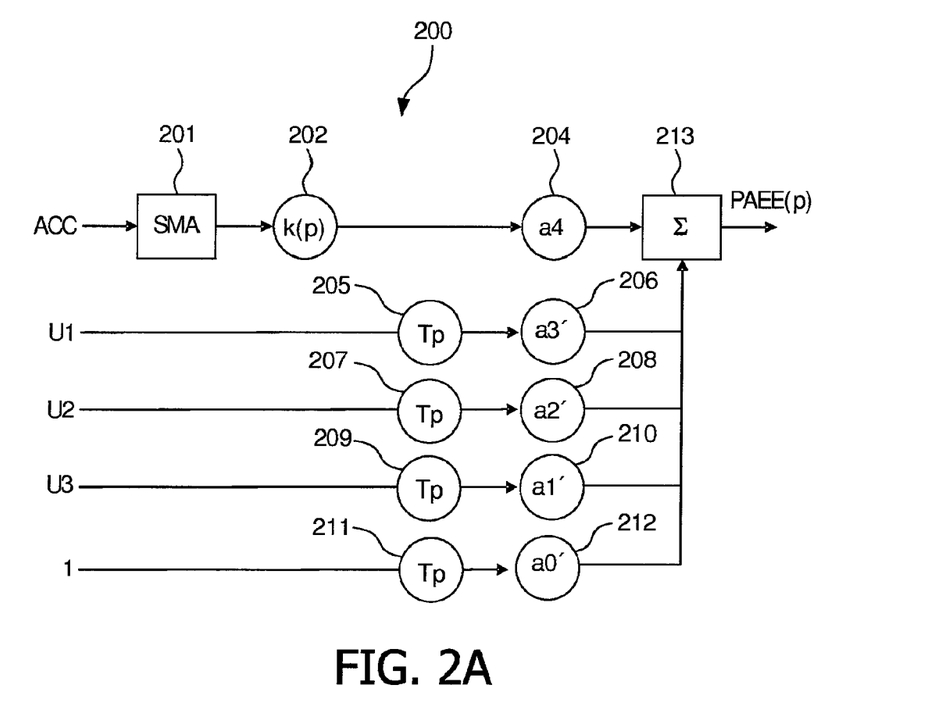
FIG. 2A shows an implementation of a model for estimating values of energy expenditure.

FIG. 2A shows an implementation 200 of equation 2, for example an implementation on a computer running a program for carrying out the diagram shown in FIG. 2. In step 201 acceleration data ACC of a given activity p is integrated or the signal magnitude area (SMA) of the acceleration data is determined, e.g. using AC(p)=$\Sigma_n \Sigma_{ti} |ACC(ti)_n|$. The result from the step 201 is multiplied with k(p) and a4 in the subsequent steps 202 and 204. User input U1, U2, U3, for example age, weight and height, are multiplied with Tp in steps 205, 207, 209 and a1', a2' and a3', respectively, in steps 206, 208 and 210. In step 213 the products from steps 201-210 are summed together with a0' multiplied by Tp provided from steps 211-212. As shown in FIG. 2A, the constant a0' may be determined by use of the value 1 as a user parameter U0.

Equation 2 only represents one possible method for determining physical activity related energy expenditure PAEE in dependence of physical activity p. In general, any number of constant parameters a1 and any number of user parameters Ui may be used instead of a1'-a3' and age, weight, and height, respectively. As an example, with N−1 user parameters Ui, a value or height 182 of physical energy related energy expenditure PAEE may be determined from:

$$PAEE(p)=\Sigma_i ai'*Tp*Ui+aN*k(p)*AC(p) \quad \text{eq. 4a}$$

or, $$PAEE(p)=\Sigma_i Tp*ai'*Ui+k(p)*AC(p), \quad \text{eq. 4b}$$

where ai' corresponds to a1'-a3' and aN corresponds a4 in eq. 2. In eq. 4b the constant parameter aN is omitted since it is included in k(p).

Accordingly, a value height 182 of the energy expenditure PAEE of a user 101 for a given activity p may be determined from acceleration data ACC and user parameters Ui,102, by determining an activity value AC(p) in dependence of activity p by integrating or summing magnitudes of the acceleration data ACC over time or time samples for the activity p, by determining a product of the activity scaling parameter k(p) and the activity value (AC(p)), and by forming a sum of the product k(p)*AC(p) with the sum of one or more user parameters Ui 102 scaled by constant parameters ai' and the period of time Tp of an activity. Thus, when only one user parameter Ui is used, the sum of products ai'*Ui reduces to a single term. The user parameters Ui may have any value including the value one corresponding to the first term Tp*a0' of equation 2.

Similarly to equation 3, the entire PAEE profile 180 of one or more activities p within a period D can be determined by forming a sequence of PAEE values 182 from equation 4a or 4b for each activity p1,p2 up to pm as follows:

$$PAEE(p1,p2, \ldots ,pm)=\{PAEE(p1), PAEE(p2), \ldots ,PAEE(pm)\}.$$

In equation 4b it is understood that the product k(p)*AC (p) is implicitly scaled by a constant parameter ai. For example, the constant parameter may be contained in the activity scaling parameter k(p) in the product k(p)*AC(p).

Figure 2B:
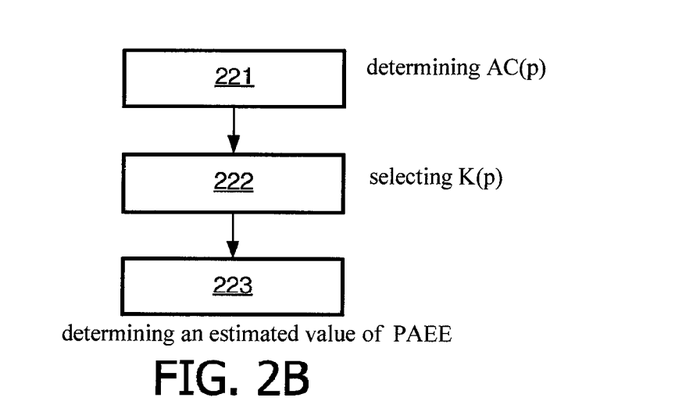
FIG. 2B is a flow-chart of a method according to the invention.

FIG. 2B shows the method steps of an embodiment of the invention for determining an energy expenditure PAEE(p) of a user 101 based on equation 4a or 4b comprising the steps:

Step 221: determining an activity value AC(p) in dependence of activity p performed by a user, by integrating or summing acceleration data ACC of the user 101 over the duration Tp of the activity p;

Step 222: selecting an activity scaling parameter k(p) from a set of scaling parameters according to the actual activity p, the scaling parameters being a function of an activity p of the user 101; and Step 223: determining an estimated value 182 of energy expenditure PAEE by obtaining a product of the activity scaling parameter k(p) and the activity value AC(p) and by forming a sum of said product k(p)*AC(p) and one or more user parameters 102 scaled by the constant parameters ai' and the duration Tp of an activity p, where the user parameters 102 characterizes the user 101.

Figure 3A:
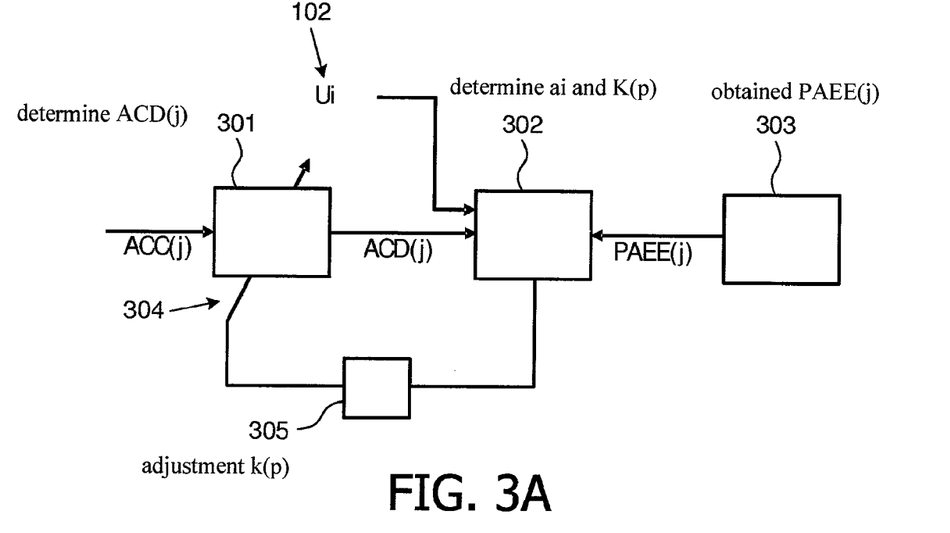
FIG. 3A shows a flow-chart for determining constant parameters and activity scaling parameters using the model.

The diagram in FIG. 3A illustrates a method to determine the constant parameters ai and the activity scaling parameters k(p) from a plurality of data pairs of measured energy expenditure values PAEE(j) and acceleration data ACC(j) of a plurality of persons or subjects j. It should be noted that subjects j used for determining parameters ai and k(p) are generally a selected group of persons whereas users (101) are users of the device 100. The measured energy expenditure values PAEE(j) are obtained from a method step 303 wherein the PAEE value is determined experimentally using a gold standard method. The acceleration data ACC for each subject j corresponds with the experimentally obtained PAEE value. In the method step 301 activity count values ACD(j) are determined from the acceleration values ACC(j).

Figure 3B:
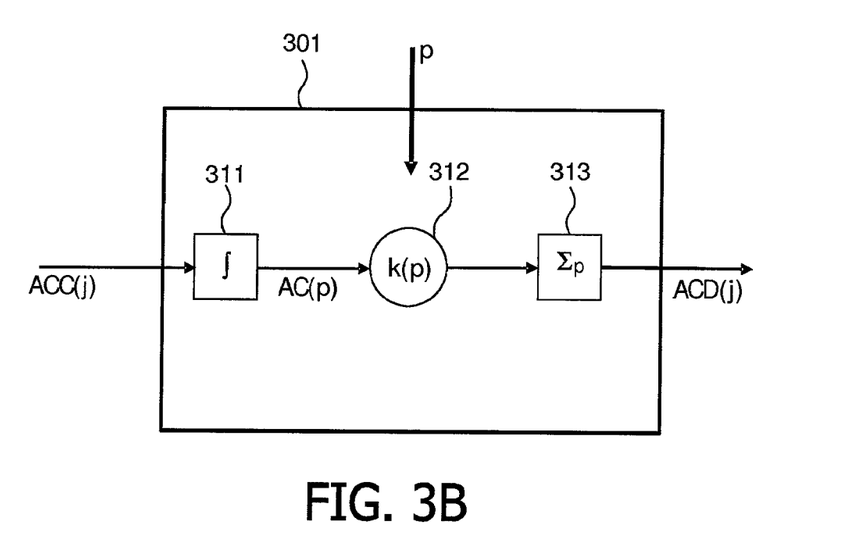
FIG. 3B shows how activity count values can be determined from acceleration values.

FIG. 3B shows how activity count values ACD(j) are determined from the acceleration values ACC(j) by integrating or summing magnitudes of the acceleration data ACC(j) over the duration Tp of an activity p to obtain values of activity count AC(p) for a given activity p in step 311. Each value of activity count AC(p) is multiplied with an activity scaling parameter k(p) in step 312. Finally, in step 313, the products of activity count values and activity scaling parameters (AC(p)*k(p)) are summed over the different activities p performed by the subject j during a given period D, for example a day. In step 311 it is understood that the integrated or summed acceleration data ACC(j) are summed over the acceleration sensor's directions if the sensor has more than one sensing direction.

In method step 302 in FIG. 3A, the constant parameters ai and the activity scaling parameters k(p) are determined using an optimization procedure. The optimization procedure is based on a given model used for calculating PAEE values. As an example the model for calculating a value of energy expenditure of activities p may be based on the equation:

$$PAEE\_CAL(j)=\Sigma_i ai*Ui+aN*ACD(j) \quad \text{eq. 6a}$$

corresponding to equation 4a or based on the equation $$PAEE\_CAL(j)=\Sigma_i ai*Ui+ACD(j) \quad \text{eq. 6b}$$

corresponding to equation 4b when one of the constant parameters ai, e.g. aN, is included in the activity scaling parameter k(p) included in the term ACD(j).

The rate of change of ai may be given by ai'=ai/D, where D is the duration over which the measured energy expenditure values PAEE(j) and the activity count values ACD(j) are determined. Thus, D may be chosen as 1440 minutes, i.e. the duration of a day.

Accordingly, by minimizing the difference between measured energy expenditure values PAEE(j) and calculated energy expenditure values PAEE_CAL(j), the constant parameters ai and the activity scaling parameters k(p) used in ACD(j) can be determined.

Minimizing the difference between measured energy expenditure values PAEE(j) and calculated energy expenditure values PAEE_CAL(j) may be performed using various methods. For example, in FIG. 3A, the constant factors ai may be determined using linear regression since eq. 6 represents a linear function of the constant parameters ai. The activity scaling parameters k(p) may be determined by iteratively adjusting k(p) using an adjustment feedback 304. For each time k(p) is adjusted, new constant factors ai are determined. The adjustment feedback 304 is used to find a set of k(p) that minimizes the aforementioned difference.

Since there may be more than one solution to the minimization problem, not only a single set of activity scaling parameters k(p), but a plurality of sets of activity scaling parameters k(p) may be found that each minimizes the difference between the measured energy expenditure values PAEE(j) and the calculated energy expenditure values PAEE_CAL(j). However, the ideal set of activity scaling parameters k(p) should not only correctly determine the accumulated energy expenditure value PAEE for activities p over a period D, but should also correctly determine the variations of the PAEE values or heights 182 for different activities p over the period D. That is, the ideal set of activity scaling parameters k(p) should correctly determine the energy expenditure profile 180 of a user for different activities p.

The correct activity scaling parameters k(p) and, thereby, the correct energy expenditure profile 180 can be determined by minimizing the difference between measured and calculated energy expenditure values PAEE involving different activities such as p,p1,p2 shown in FIG. 1. Alternatively, the correct activity scaling parameters k(p) can be determined by calculating a so-called Pearson's coefficient $R^2$ where a high value of the Pearson's coefficient $R^2$ indicates that equation 6 gives, on average, a good prediction of the actual measured PAEE(j). Pearson coefficient $R^2$ may be defined as $$R^2 = 1 - \frac{\sum_j [PAEE(j) - PAEE\_CAL(j)]^2}{\sum_j [PAEE(j) - \overline{PAEE(j)}]^2}$$

where $\overline{PAEE(j)}$ is the average over j of the measured PAEE(j). It can be seen that the term $\Sigma_j[PAEE(j) - PAEE\_CAL(j)]^2$ in $R^2$ is the aforementioned calculation difference, so a good prediction would lead to an $R^2$ value that approaches to one.

Accordingly, an initial set of activity scaling parameters k(p) may be used as an initial guess. After the Pearson's coefficient $R^2$ has been calculated a new set of parameters k(p) may be determined by adjusting the values of the k(p) parameters on basis of the value of the Pearson's coefficient $R^2$.

The optimum values of k(p) may also be determined using a global searching, where for pre-set ranges of values of k(p)'s $R^2$ is computed, and the set of k(p) resulting in the highest $R^2$ is chosen.

The adjustment of the activity scaling parameters k(p) may be adjusted so that an activity scaling parameter k(p) is adjusted to a value greater than a preset threshold value, e.g. the value one, for activities having activity values AC(p) which underestimates the actual energy expenditure PAEE, and so that an activity scaling parameter k(p) is adjusted to a value smaller than the preset threshold value for activities having activity values AC(p) which overestimates the actual energy expenditure PAEE. In general, when the constant parameter a4 or aN is included in k(p), the preset threshold is different from the value one, and when a4 or aN is not included in k(p) the preset threshold may be equal to the value one.

Thus, the activity scaling parameters k(p) are determined by minimizing the difference between a measured energy expenditure value for a given period D, e.g. a day, and a sum of values of the estimated energy expenditure values for activities p over the same period D.

Therefore, an advantage is obtained by using activity scaling parameters k(p) which have been experimentally determined under the constraint that the sum of values of the estimated energy expenditure values for activities p during a period D approximates the measured energy expenditure value measured over the same period D. That is, the determined activity scaling parameters k(p) have the property of up-scaling activity values AC(p) which underestimates the actual energy expenditure PAEE due to acceleration values which are too low to reflect the actual energy expenditure. Similarly, the activity scaling parameters k(p) have the property of down-scaling activity values AC(p) which overestimates the actual energy expenditure PAEE due to acceleration values which are too high to reflect the actual energy expenditure. A further advantage is that the total accumulated estimated energy expenditure over a day approximates the actual measured energy expenditure of a day since the activity scaling parameter k(p) have been determined under the constraint that the estimated total energy spent of the day remains unchanged in comparison with the total measured energy.

The minimization of the difference between measured and calculated energy expenditure profiles, e.g. by calculation of the Pearson's coefficient $R^2$, and the adjustment of activity scaling parameters k(p) may be performed in a method step 305 in the adjustment feedback 304.

It is understood that the method for determining the constant parameters ai and the activity scaling parameters k(p) is not performed during use of the device 100 for determining an energy expenditure of a user 101, but is performed in connection with the manufacturing of the energy expenditure device 100. Thus, the ai and k(p) parameters determined using for example the process shown in FIG. 3A-B, may be applied to the energy expenditure devices 100 during assembly, for example by storing the parameters in a memory of the device 100.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A device for determining an energy expenditure of a user of a plurality of users performing a plurality of activities, the device comprising:
  one or more ports for receiving acceleration data of the user as a function of time and one or more user parameters characterizing the user, wherein the acceleration data represents movement of an accelerometer device worn by the user;
  a display device;
  a memory having instructions stored therein and having constant parameters and scaling parameters representing a function of respective ones of the plurality of activities performed by the user stored thereon wherein the instructions include:
  instructions for defining a single mathematical model for estimating energy expenditure, wherein the single mathematical model processes input acceleration data using the constant parameters to produce an output estimation of energy expenditure; and
  a processor in communication with the display device, a Global Positioning System (GPS) sensor carried by the user, and the memory having the instructions, the constant parameters and the scaling parameters stored therein, wherein the processor is configured to execute the instructions stored in the memory to perform the acts of:
    obtaining measurement of energy expenditure values and acceleration data over a predetermined period wherein the acceleration data represents movement of respective other accelerometer devices worn by a plurality of users, calculating by the processor values of energy expenditure of activities of the plurality of users in a loop to determine the constant parameters and scaling parameters in accordance with the single mathematical model;

minimizing by the processor a difference between the measurement of energy expenditure values and the calculated energy expenditure values by obtaining an activity count value for each data pair of the measurement of energy expenditure values and the acceleration data over the predetermined period of each user of the plurality of users by accumulating a product of the scaling parameters and activity values over the activities during the predetermined period;

determining by the processor an energy expenditure of a current activity of the plurality of activities performed by the user wearing the accelerometer device by:

accumulating, from the accelerometer device, current acceleration data of the current activity from the user for a duration of the current activity, identifying the current activity as cycling based on velocity data received from the GPS sensor in conjunction with the current acceleration data of the current activity, wherein the identifying is based on comparisons of the velocity data to a first threshold and the current acceleration data to a second threshold;

selecting a scaling parameter of the scaling parameters that is associated with cycling, and applying the single mathematical model, including scaling the current acceleration data using the selected scaling parameter, to obtain an energy expenditure estimate associated with the cycling current activity, whereby the scaling parameters adapt application of the single mathematical model to human-worn accelerometer data generated according to any of the plurality of activities; and rendering a graphical user interface on the display device, wherein the graphical user interface comprises energy expenditure estimates associated with the user wearing the accelerometer device.

2. The device according to claim 1, wherein the scaling parameters are greater than a threshold value for the activities having the activity value determined from the acceleration data which underestimates an actual energy expenditure, and wherein the scaling parameters are smaller than the threshold value for the activities having the activity value determined from the acceleration data which overestimates the actual energy expenditure.

3. The device according to claim 1, wherein the processor is further configured to execute the instructions stored in the memory to determine a time profile of actual energy expenditure values based on the energy expenditure estimates.

4. The device according to claim 1, wherein the one or more user parameters include age, weight and height, and an accumulation of said product and the one or more user parameters are scaled by the constant parameters and the duration of the current activity.

5. The device according to claim 1, further comprising an acceleration sensor for measuring the acceleration data of the user in one or more acceleration directions, wherein the activity value of the current activity is determined by accumulating the acceleration data of the user over the duration of the activity for each of the one or more acceleration directions of the acceleration sensor.

6. The device of claim 1, wherein identifying the current activity as cycling is further based on data from a microphone.

7. The device of claim 1, wherein identifying the current activity as cycling is further based on data from a heartbeat sensor, a blood pressure sensor and a microphone.

8. A device for determining an energy expenditure of a user performing a plurality of activities, the device comprising:

one or more ports for receiving acceleration data of the user as a function of time and one or more user parameters characterizing the user, wherein the acceleration data represents movement of an accelerometer device worn by the user, a display device;

a memory having instructions stored therein and having constant parameters and scaling parameters representing a function of respective ones of the plurality of activities performed by the user stored thereon wherein the instructions include:

instructions for defining a single mathematical model for estimating energy expenditure, wherein the single mathematical model processes input acceleration data using the constant parameters to produce an output estimation of energy expenditure; and a processor in communication with the display device, a Global Positioning System (GPS) sensor carried by the user, and the memory having the instructions, the constant parameters and the scaling parameters stored thereon, wherein the processor is configured to execute the instructions stored in the memory to perform acts of:

transforming by the processor the acceleration data accumulated over duration of a current activity of the plurality of activities performed by the user into an activity value of the current activity performed by the user, identifying the current activity as cycling based on velocity data received from the GPS sensor in conjunction with current acceleration data of the current activity, wherein the identifying is based on comparisons of the velocity data to a first threshold and the current acceleration data to a second threshold;

estimating by the processor an energy expenditure value by adding at least one of the user parameters scaled by the constant parameters and the duration of the current activity to a product of the scaling parameter of the plurality of scaling parameters that is associated with cycling and the activity value, and rendering a graphical user interface on the display device, wherein the graphical user interface includes, as part of a temporal sequence of estimated values of energy expenditure for different activities of the plurality of activities, graphical indications of the cycling and the energy expenditure of the cycling;

wherein the scaling parameters are determined by minimizing a difference between a measured energy expenditure value obtained for a predetermined period comprising one or more activities of the plurality of activities and an accumulation of estimated energy expenditure values for the one or more activities over the predetermined period, and wherein the difference is minimized using the single mathematical model by accumulating acceleration data over a duration of an activity and producing and accumulating products of the accumulated acceleration data and the scaling parameters, whereby the scaling parameters adapt application of the single mathematical model to human-worn accelerometer data generated according to any of the plurality of activities.

9. The device of claim 8, wherein the scaling parameters are determined from a plurality of pairs of measured energy expenditure values and acceleration data of a plurality of users measured over a predetermined period.

10. A method for determining an energy expenditure of a user on a portable device having at least one input port, a processor, and a memory having instructions stored thereon, wherein the processor executes the instructions to determine the energy expenditure, the method comprising acts of:
  obtaining a current activity performed by the user using one of data entry and an automatic activity recognition algorithm, wherein the automatic activity recognition algorithm identifies the current activity as cycling based on velocity data received from a Global Positioning System (GPS) sensor in conjunction with acceleration data representing movement of an accelerometer device worn by the user, wherein the identification by the automatic activity recognition algorithm is based on comparisons of the velocity data to a first threshold and the acceleration data to a second threshold;
  transforming by the processor the acceleration data accumulated over a duration of the current activity into an activity value of the current activity performed by the user;
  selecting by the processor a scaling parameter associated with cycling from a plurality of scaling parameters stored in the memory, each of the plurality of scaling parameters being a function of a possible activity of the user and the selected scaling parameter being a function of the current activity of the user;
  determining by the processor an estimated energy expenditure value by adding at least one of user parameters multiplied by the constant parameters and by the duration of the current activity to a product of the selected scaling parameter and the activity value; and
  rendering a graphical user interface on the display device, wherein the graphical user interface includes graphical indications of the cycling and the estimated energy expenditure value,
  wherein the plurality of scaling parameters is determined by minimizing a difference between a measured energy expenditure value obtained for a predetermined period comprising one or more activities of the plurality of activities and an accumulation of estimated energy expenditure values for the one or more activities over the predetermined period, and
  wherein the difference is minimized using a single mathematical model stored in the memory by accumulating acceleration data over a duration of an activity and producing and accumulating products of the accumulated acceleration data and the scaling parameters, whereby the scaling parameters adapt application of the single mathematical model to human-worn accelerometer data generated according to any of the plurality of activities.

11. The method of claim 10, wherein the automatic activity recognition algorithm identifies the current activity as cycling further based on data from a microphone.

12. The method of claim 10, wherein the automatic activity recognition algorithm identifies the current activity as cycling further based on data from a heartbeat sensor, a blood pressure sensor and a microphone.

13. A device for determining an energy expenditure of a user of a plurality of users performing a plurality of activities, the device comprising:
  one or more ports for receiving acceleration data of the user as a function of time and one or more user parameters characterizing the user, wherein the acceleration data represents movement of an accelerometer device worn by the user;
  one or more output components;
  a memory having instructions stored therein and having constant parameters and scaling parameters representing a function of respective ones of the plurality of activities performed by the user stored thereon wherein the instructions include:
  instructions for defining a single mathematical model for estimating energy expenditure, wherein the single mathematical model processes input acceleration data using the constant parameters to produce an output estimation of energy expenditure; and
  a processor in communication with the one or more output components, a Global Positioning System (GPS) sensor carried by the user, and the memory having the instructions, the constant parameters and the scaling parameters stored therein, wherein the processor is configured to execute the instructions stored in the memory to perform the acts of:
    obtaining measurement of energy expenditure values and acceleration data over a predetermined period wherein the acceleration data represents movement of respective other accelerometer devices worn by a plurality of users,
    calculating by the processor values of energy expenditure of activities of the plurality of users in a loop to determine the constant parameters and scaling parameters in accordance with the single mathematical model;
    minimizing by the processor a difference between the measurement of energy expenditure values and the calculated energy expenditure values by obtaining an activity count value for each data pair of the measurement of energy expenditure values and the acceleration data over the predetermined period of each user of the plurality of users by accumulating a product of the scaling parameters and activity values over the activities during the predetermined period;
    determining by the processor an energy expenditure of a current activity of the plurality of activities performed by the user wearing the accelerometer device by:
      accumulating, from the accelerometer device, current acceleration data of the current activity from the user for a duration of the current activity,
      identifying the current activity as cycling based on velocity data received from the GPS sensor in conjunction with the current acceleration data of the current activity, wherein the determining is based on comparisons of the velocity data to a first threshold and the current acceleration data to a second threshold;
      selecting a scaling parameter of the scaling parameters that is associated with cycling, and
      applying the single mathematical model, including scaling the current acceleration data using the selected scaling parameter, to obtain an energy expenditure estimate associated with the cycling current activity, whereby the scaling parameters adapt application of the single mathematical model to human-worn accelerometer data generated according to any of the plurality of activities; and rendering, at one or more of the output components, indications of the cycling and the energy expenditure estimate of the cycling.

* * * * *